(12) United States Patent
Jasper

(10) Patent No.: US 10,368,962 B2
(45) Date of Patent: Aug. 6, 2019

(54) METHOD AND APPARATUS FOR ORTHODONTIC CORRECTIONS

(71) Applicant: James Joseph Jasper, Portland, OR (US)

(72) Inventor: James Joseph Jasper, Portland, OR (US)

(*) Notice: Subject to any disclaimer, the term of this patent is extended or adjusted under 35 U.S.C. 154(b) by 0 days.

(21) Appl. No.: 16/142,900

(22) Filed: Sep. 26, 2018

(65) Prior Publication Data

US 2019/0021821 A1    Jan. 24, 2019

Related U.S. Application Data

(63) Continuation-in-part of application No. 15/356,925, filed on Nov. 21, 2016, now abandoned, and a continuation-in-part of application No. 15/843,414, filed on Dec. 15, 2017.

(51) Int. Cl.
    *A61C 7/36*    (2006.01)
    *A61C 7/08*    (2006.01)

(52) U.S. Cl.
    CPC . *A61C 7/36* (2013.01); *A61C 7/08* (2013.01)

(58) Field of Classification Search
    CPC .................................. A61C 7/08; A61C 7/36
    USPC ........................................................ 433/8–17
    See application file for complete search history.

(56) References Cited

U.S. PATENT DOCUMENTS

| | | | |
|---|---|---|---|
| 2011/0195370 A1* | 8/2011 | Griffiths | A61C 7/00 433/6 |
| 2013/0236849 A1* | 9/2013 | Jasper | A61C 7/36 433/19 |
| 2015/0086935 A1* | 3/2015 | Paul | A61C 7/00 433/6 |
| 2016/0067014 A1* | 3/2016 | Kottemann | A61C 7/36 433/6 |
| 2016/0120624 A1* | 5/2016 | Yousefian | A61C 7/282 433/17 |
| 2017/0252127 A1* | 9/2017 | Yousefian | A61C 7/18 |

* cited by examiner

*Primary Examiner* — Ralph A Lewis
(74) *Attorney, Agent, or Firm* — Mark S Hubert

(57) ABSTRACT

An improved dental apparatus that can treat Class II or Class III malocclusions without the need for braces, that can be repaired outside of the patient's mouth, that can be temporarily removed by the patient, that can be fitted, calibrated, set up and adjusted outside the patient's mouth prior to installation, and that is inexpensive. It utilizes universal torsion springs with accurate bending forces assembled with linear members of varying lengths to make a curved intrusive vector force device connecting teeth aligners that apply gentle constant forces to correct underbite and overbite conditions.

10 Claims, 8 Drawing Sheets

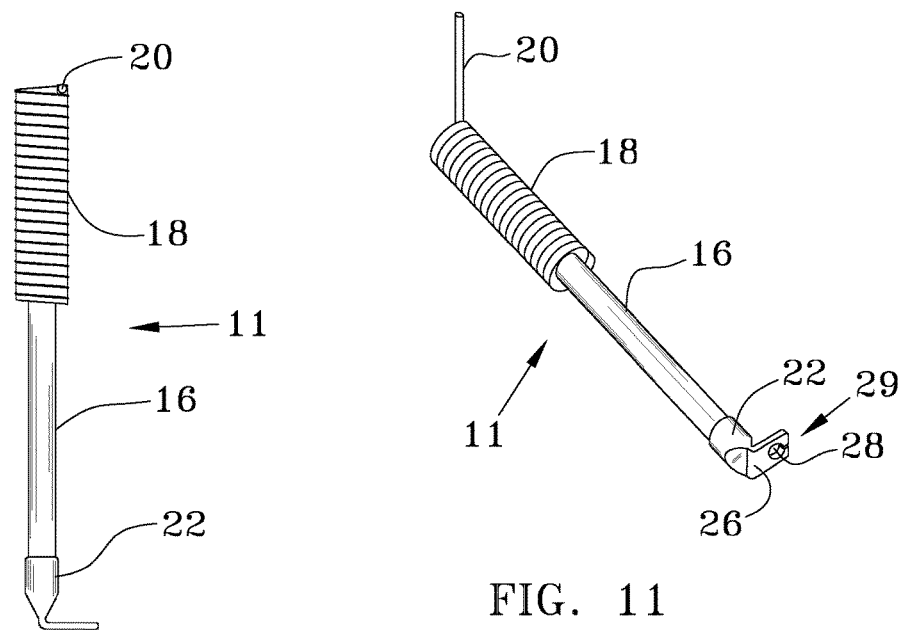
FIG. 11
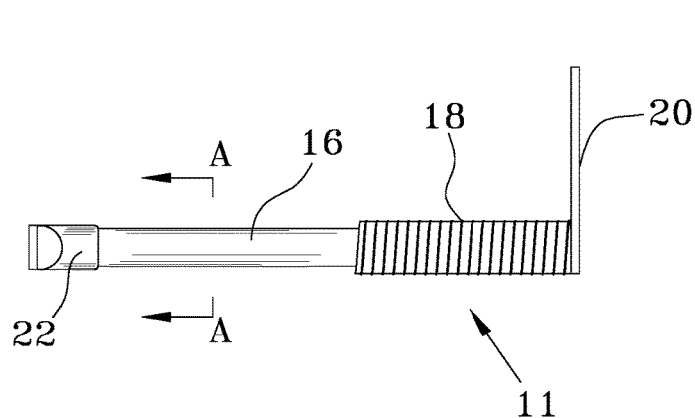
FIG. 12
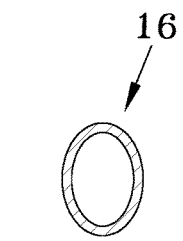
FIG. 13
FIG. 10

METHOD AND APPARATUS FOR ORTHODONTIC CORRECTIONS

CLAIM FOR DOMESTIC PRIORITY

This application incorporates herein by reference and is a Continuation in Part of U.S. patent application Ser. No. 15/356,925 filed Nov. 21, 2016, entitled "Orthodontic Vector Force Application Apparatus." This application also incorporates herein by reference and is a Continuation in Part of U.S. patent application Ser. No. 15/843,414 filed Dec. 15, 2017, entitled "Method and Apparatus for Applying Curved Vector Forces for Orthodontic Corrections."

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to orthodontic appliances, and more particularly to the technology of pre-calibrated and sized, curved vector force application devices for the correction of the misalignment of teeth between the upper dental arch and lower dental arch, whether it be overbite or underbite.

BACKGROUND

The incorrect positioning of teeth or the misalignment of teeth between the upper dental arch and lower dental arch are known as malocclusions. Malocclusions are categorized by dental health professionals in three classifications: Class I—the jaw relationship is normal but individual teeth (whether located on the upper or lower dental arch) have problems such as spacing, crowding, etc., and do not achieve a good fit with the corresponding teeth on the opposite arch. Class II—commonly referred to as an overbite, the upper jaw is not in proper position, and an increased projection of the upper teeth in front of the lower teeth results. This lack of contact between the front teeth allows them to keep erupting or extruding, from the gum line into the mouth until they contact something, usually the palate. This over-extrusion, especially of the lower front teeth, requires the orthodontist to place intrusive forces on these teeth during treatment. Finally, Class III—wherein the upper dental arch rests behind the lower dental arch when the mouth is closed, commonly referred to as an underbite.

Class 1 malocclusions are treated with braces (that is the combination of brackets, placed on individual teeth, and an archwire connecting each of the brackets) that are gradually adjusted to urge the movement of the teeth into their desired positions over a period of months or years. Class II or III malocclusions are also corrected slowly over an extended period of time, but by a vector force application apparatus that applies a low pulling or pushing pressure vector force to the offending jaw into its proper bite position. This vector appliance thus actually forces the jawbones and muscles to physically adapt or "learn" the correct bite positioning. Since commonly, Class I malocclusions are found in patients that also have Class II or Class III malocclusions, these misalignments of jaws and teeth are treated together wherein the brackets and/or archwires of the braces serve as the anchor point for the vector appliance.

There was a bite-correcting appliance known as the stainless steel "Jasper Jumper" that gained popularity because of its low cost, adjustability, ease to repair and mostly because its results are garnered easily and in a short period of time. This is discussed in detail in U.S. Pat. No. 4,708,646. This was a non-removable bite-correcting appliance secured to braces. This prior art patent also teaches a linear force appliance on a retainer. (FIG. 17) The problem with this prior art device was that the linear forces pushing up on the distal of the retainer, caused the front part of the retainer to fall out of the mouth. This appliance was never marketed and was prone to structural failure (coil breakage) because the stainless-steel parts work hardened during the thousands of times the patient opened and closed their mouth during the corrective period. There were subsequent advances in this technology as detailed in U.S. Pat. Nos. 8,529,253, 8,721,326 and 8,905,755 incorporated herein by reference.

These devices, known as braces, have drawbacks in that they are costly, labor intensive for the dentist and require frequent visits to the orthodontist for fittings, adjustments and repair. Also, once installed, these remained with the patient until removed by the orthodontist. This often precluded the wearer from participating in sports for period of time. Physical oral intimacy was also compromised. Furthermore, failures in the appliance required in-mouth repairs by an orthodontist which is costly, time consuming, uncomfortable and expensive.

Henceforth, an improved dental apparatus that can treat Class II or Class III malocclusions without the need for braces, that can be repaired outside of the patient's mouth, that can be temporarily removed by the patient, that can be fitted, calibrated, set up and adjusted outside the patient's mouth prior to installation, and that is inexpensive, and that aid in retaining the retainers on the patient's teeth, would fulfill a long-felt need in the dental industry. This new invention utilizes and combines known and new technologies in a unique and novel configuration to overcome the aforementioned problems and accomplish this.

BRIEF SUMMARY

In accordance with various embodiments, an orthodontic apparatus for the treatment of Class II and III malocclusions by the application of curved rather than linear intrusive vector forces is provided that can be temporarily removed by the user for sports, eating, intimacy and sleep; that can be repaired and cleaned outside of the mouth; that can be configured with either full or partial anchor sheaths; that do not require the use of braces affixed to the teeth; that have an optimal, pre-set, calibrated corrective curved intrusive vector force pressure range of 3.5 ounces of pushing force; that can be used with bracing-only aligners that are not designed for any "crowding" correction; that can be removed to accommodate other dental or mouth work; that offers minimal discomfort for the patient; that gives visual indication of decreased corrective pressure; that can be pre-configured before installation outside the patient's mouth; and most importantly, that can impart tipping forces that aid in the retention of the device on the patient's teeth, and that offers a huge reduction in cost by reduced orthodontist visits.

This bite-correcting orthodontic appliance is made with large 0.039 Nickel Titanium alloy coils that are break resistant and also attach directly to the elements of braces (i.e., brackets and archwires); flex with a preset pressure of 3.5 ounces when bent to approximately 90 degrees in the distal 25-45% of their overall appliance length, to stay away from the food bolus; have a reduced profile for patient comfort; and introduce gentle intrusive force vectors to the patient's upper and lower teeth that are not along the appliance's axis but instead sweep in an arch to rotate up on the front of the upper molars. These molars are connected to the front teeth with a large stainless-steel wire, thus transmitting intrusive forces directly to the over erupted front teeth via the archwire. The lower front teeth are also intruded via the lower arch wire, as the appliances try to return to their preinstalled (passive) state. The result is rapid, yet gentle changes, that have the unexpectedly result of reducing treatment times significantly. Usually full correction can be accomplished in four months or less.

In this case, the utility or function of the curved vectors is to simply hold the retainers in the mouth. It is not able to intrude the anterior teeth as there are no arch wires connected to the front teeth. The curved vectors that hold the loose-fitting retainers onto the teeth, is the opposite of prior art linear vectors pushing up on the back end of the retainers that make them fall out. This unexpected result of curved vectors mated to removable retainers treats malocclusions without braces and in record time.

Various modifications and additions can be made to the embodiments discussed without departing from the scope of the invention. For example, while the embodiments described above refer to particular features, the scope of this invention also includes embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components.

FIG. 10 is a top view of the orthodontic vector force application means;

FIG. 11 is a right-side perspective view of the orthodontic vector force application means;

FIG. 12 is a left-side view of the orthodontic vector force application means;

FIG. 13 is an enlarged cross-section taken at the line designated A-A on FIG. 12;

DETAILED DESCRIPTION OF CERTAIN EMBODIMENTS

Figure 1:
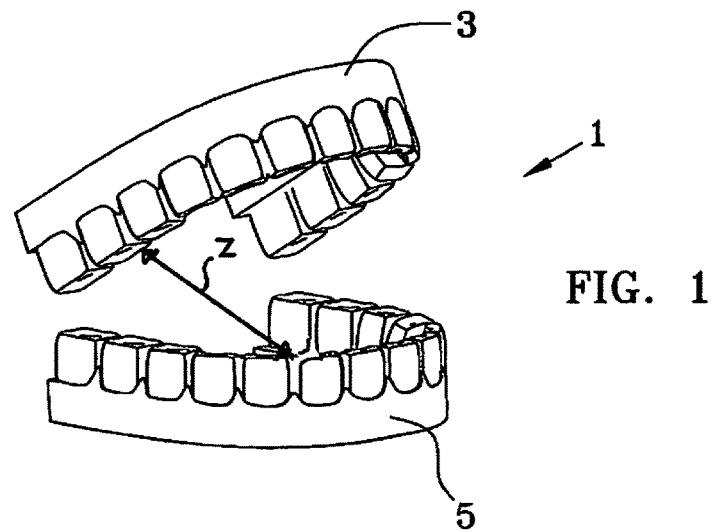
FIG. 1 is a left-side perspective view of an open dental model.

While various aspects and features of certain embodiments have been summarized above, the following detailed description illustrates at least on exemplary embodiment in further detail to enable one skilled in the art to practice such an embodiment. The described example is provided for illustrative purposes and is not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. While various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

In this description, the directional prepositions of up, upwardly, down, downwardly, front, back, top, upper, bottom, lower, left, right and other such terms refer to the device as it is oriented and appears in the drawings and are used for convenience only; they are not intended to be limiting or to imply that the device has to be used or positioned in any particular orientation. Distal in all instances shall refer to components or component parts located at the back of the mouth and proximal shall refer to components or component parts located at the front of the mouth.

Unless otherwise indicated, all numbers herein used to express quantities, dimensions, and so forth, should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

As used herein, the term "curved intrusive vector force application means" is to be interpreted according to 35 USC § 112 [para] 6. It refers to a component of an orthodontic device that applies a curved or arced pushing force that can be transmitted to the upper and lower dental arches for the correction of Class II or Class III malocclusions.

As used herein the term "aligner" refers to a series of polymer sheaths, custom fit over a patient's teeth, with slightly different corrective tooth positions therein. When worn in a timed sequence they will gradually straighten the teeth. Their primary purpose is to move (correct or straighten) some or all of the upper and lower teeth in the mouth and relative to each other for the treatment of Class I malocclusions.

As used herein the term "anchor sheath" refers to a removable polymer sheath (also known as a retainer) that is custom fit for frictional engagement over all or some of the teeth passively in the upper arch and lower arch teeth sets. Its purpose is to allow the teeth to serve as anchor points for the attachment of an orthodontic curved intrusive vector force application means used for the treatment of Class II or Class III malocclusions, thereby allowing the curved intrusive vector forces of the apparatus to be applied to the jaws. They retain the teeth in the configuration they are in as they offer no corrective action to the teeth themselves. Their purpose (generally in about 95% of malocclusions) is to posture the lower jaw forward to overcome underbite so as to allow the end of the mandible (the condyle) to grow and thus make the lower jaw grow forward to correctly meet the upper front teeth.

The term "curved intrusive vector force application apparatus" as used herein is a removable, adjustable force orthodontic device comprised of a curved intrusive vector force application means, operably attached to a pair of upper dental arch and lower dental arch anchor sheaths.

The term "ounces of pressure" or "ounces" as used herein refer to the numerical value of the curved vector forces generated between the attachment points (the distal and proximal ends of the torsion spring) when the torsion spring is bent to approximately 90 degrees (plus or minus 5 degrees).

The present invention relates to a novel design for a removable, adjustable curved intrusive vector force application means mated to a removable custom fit sheath, anchored onto the outer faces of all or some of the teeth comprising the upper and lower dental arches. Its novelty lies in the facts that it arrives pre-calibrated at 3.5 ounces of corrective pressure and ready to wear after initial dental measurements, imparts curved vector corrective forces onto a removable set of dental retainers whereas all prior art devices impart linear forces onto dental retainers or aligners, allows the dentist to control the corrective forces exerted on the jaws rather than that of the patient's jaw; is force limited to 3.5 ounces of corrective pressure by the torsion spring design and as an unexpected result imparts a tipping pressure that aids in retaining the retainers onto the patients teeth whereas the prior art linear force retainers tend to eject the top retainer or aligner when excessive bite pressure is exerted from the patients jaws.

Figure 14:
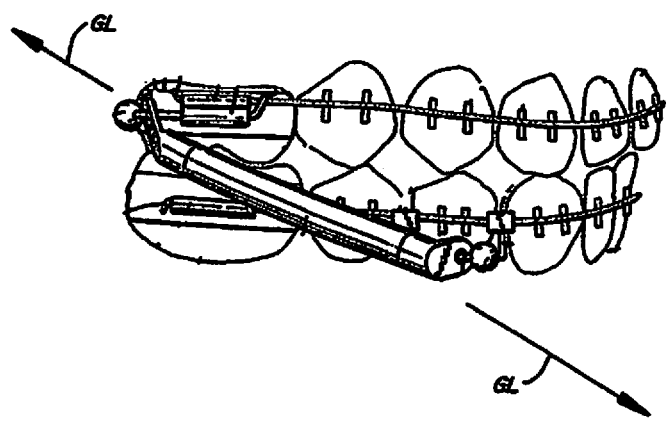
FIG. 14 is an example of a prior art orthodontic linear vector force application apparatus.

Mechanical devices to impart linear vector forces on both braces and also on anchor sheaths (also known as removable retainers) are well documented in the 30-year old U.S. Pat. No. 4,708,646 by the present inventor. (Hereinafter the '646 patent.) This prior art utilized elongated linear members anchored onto both the patient's teeth or anchor sheaths to impart linear vectors of force onto the jaws of the patient to correct overbite situations. These vector forces can best be seen looking at the force lines designated GL on FIG. 14 from the prior art '646 patent of Dr. Jasper.

Figure 15:
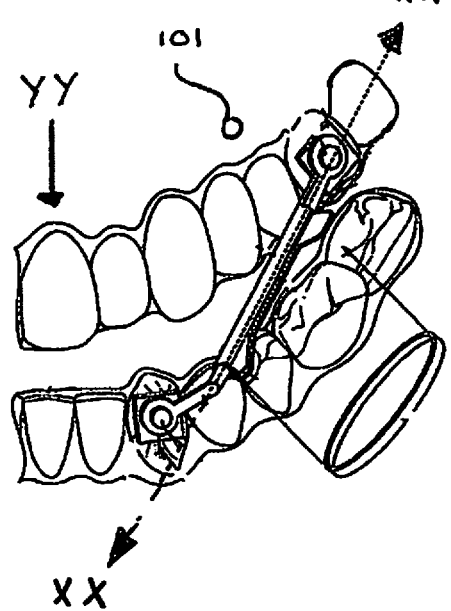
FIG. 15 is another example of a prior art orthodontic linear vector force application apparatus.

The device worked well when coupled to the teeth directly (braces) and became known industry wide as the "Jasper Jumper". However, it did not work on anchor sheaths (plastic aligners) because the line of the vector force applied was linear and caused the upper jaw to tip and the front of the anchor sheath to dislodge. Simply stated, there was not enough gripping force in the anchor sheath to overcome the vector forces for overbite correction and as a result the plastic aligners would dislodge from the anterior teeth. Another example of such linear vector forces XX applied to anchor sheaths through linear members, for orthodontic correction of overbite, can be seen in FIG. 15, US Patent Application 2016/0067014, to Kottemann.

The use of rigid metal rods as linear members for generating linear vector forces between the upper and lower dental arches has several drawbacks when coupled with removable aligners or retainers. (See Patent Application 2016/0067014, to Kottemann, FIG. 15) Here, linear forces are put on the lower and upper dental arches to straighten the teeth or to correct class II or III malocclusions. When mated with aligners or retainers, these linear forces applied towards the back of the dental arches cause resulting downward forces YY at the front of the top dental arch that dislodge the device about the center of rotation 101. This occurs when the patient bites down too hard. The amount of this dislodging force is controlled by the patient—not the dentist. The harder the patient bites, (25 pounds force or greater) the more dislodging that will occur as the bite force of the jaws are transmitted through the rigid, steel, linear force dental correction device. Simply stated, the mating of linear force dental correction devices with aligners will not work efficiently to correct class II or III malocclusions.

Figure 16:
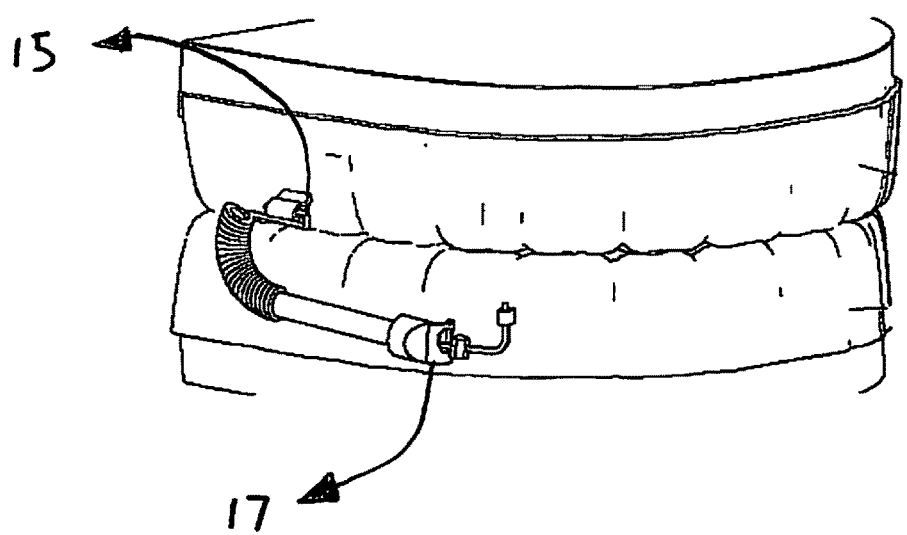
FIG. 16 is a perspective view of the curved intrusive vector forces applied through anchor sheaths.
Figure 17:
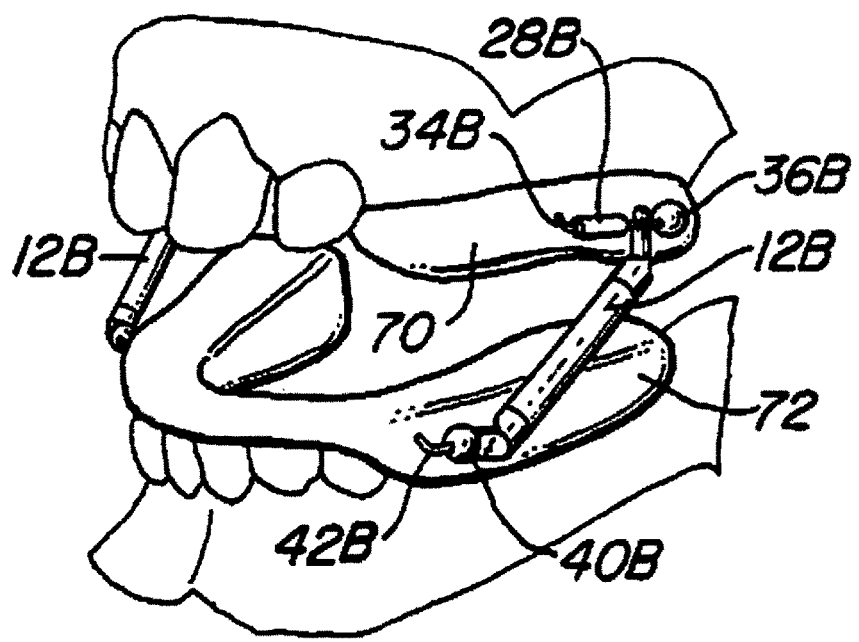
FIG. 17 is a perspective view of prior art linear forces applied to retainers.

The present curved intrusive vector force device applies curved intrusive vectors into use with retainers (anchor sheaths) so as not to not tip the upper jaw and keep the aligner on the teeth so that the device can do its job while the 3.5 ounces of corrective forces corrects the overbite condition by growing the lower jaw. This novel difference can be seen in the sweeping arcs of the applied vector forces as rays 15 and 17 of FIGS. 5 and 16. Thus, the introduction and mating of curved intrusive force vectors onto anchor sheaths while implementing the proper corrective pressures also has the unexpected result of helping the anchor sheaths stay on the patient's teeth so they can do their intended job of correcting the dental malocclusions. Basically, the curved vectors of present apparatus hold the aligners in place while the preset 3.5 ounce return force torsion spring postures the jaw forward for correction.

Although the mating of corrective dental appliances with straight line vector forces onto aligners has been taught in the referenced prior art of Kottemann (US 2016/0067014) and decades ago by the present inventor himself, the use of such appliances that impart curved intrusive vectors has not. It is a novel concept that allows the aligners to stay in place while the arced, sweeping direction of the device's applied forces gently urge the jaws into the correct alignment.

Further, research has shown that a gentle application of approximately 3.5 ounces of constant pressure (plus or minus one half ounce) between the patient's upper dental arch and lower dental arch with a properly sized orthodontic curved intrusive vector force application apparatus can correct most Class II or III malocclusions in four months.

With the present device, no matter how hard the patient bits down, there will still only be 3.5 ounces of force posturing the jaw forward.

FIG. 1 shows a perspective view of the upper dental arch 3 and the lower dental arch 5 of the dental model 1. The upper anchor sheath 40 and lower anchor sheath 42 (FIG. 2) are tightly form fitted sheaths that encapsulate the other surfaces of some or all of the teeth in the dental arches with a thin layer of medical grade polymer (preferably clear). These can be made in two different ways. With the older, conventional method the patient's teeth are imprinted into a quick set gel in a tray, then a hard casting of this imprint is made from which the matingly conformed polymer sheath is made with the guide wire imbed anchors 32, and attachment wire imbed anchors 34 cast therein at the appropriate locations. (Alternatively the guide wire alone may be cast into the anchor sheaths.) In the modern way, there is an accurate 3D image taken of the patient's teeth with a scanner which is sent to a 3D printer that builds a sheath that perfectly conforms to the outer surface of the teeth, again with the imbed anchors 32 and 34 or guide wire and any reinforcing elements formed therein.

The anchor sheaths are slightly flexible to accommodate their installation and removal, and are generally made from a set of castings taken of the user's teeth. The thickness of the anchor sheaths varies at different points and are thickened or reinforced in the regions 41, 43 and 45 where the guide wire imbed anchors 32, and attachment wire imbed anchors 34 are placed as necessary to ensure a secure affixation and so that the imbeds cannot wear their way through the sheaths. (FIG. 2)

Referring generally to FIGS. 2-9 two embodiments of an orthodontic curved intrusive vector force application apparatus 10 (FIG. 3) (hereinafter "apparatus") according to the present invention, is connected to both the upper dental arch 3 (maxillary jaw) and the lower dental arch 5 (mandibular jaw) by placement of their anchor sheaths 40 and 42 over the teeth of the upper and lower dental arches 3 and 5. Each anchor sheath 40 or 42 may be formed to fit the patient's mouth and extend over whatever number of teeth are required to provide a firm anchor for the sweeping, arced pushing forces used to facilitate the correction desired.

Figure 2:
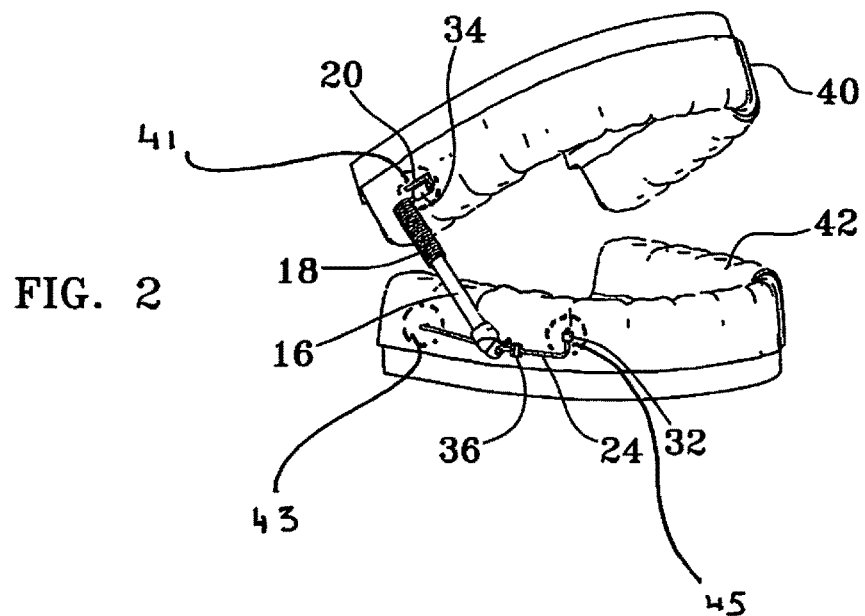
FIG. 2 is a left-side perspective view of the orthodontic vector force application apparatus installed on an open dental model for overbite correction.
Figure 3:
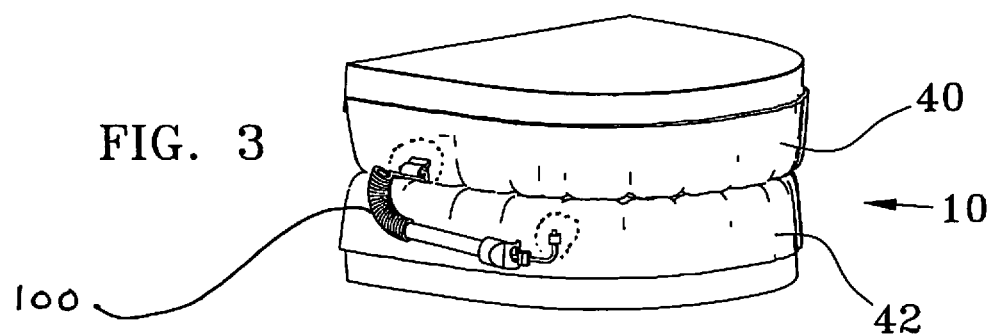
FIG. 3 is a left-side perspective view of the orthodontic vector force application apparatus installed on a closed dental model for overbite correction.
Figure 4:
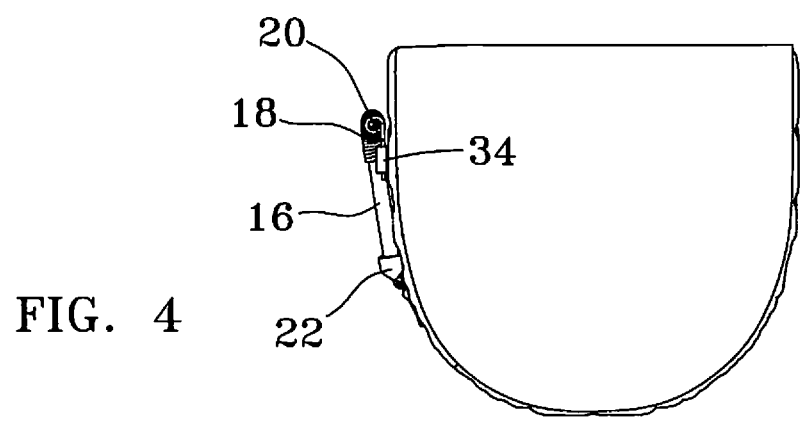
FIG. 4 is a top view of the orthodontic vector force application apparatus installed on a closed dental model for overbite correction.
Figure 6:
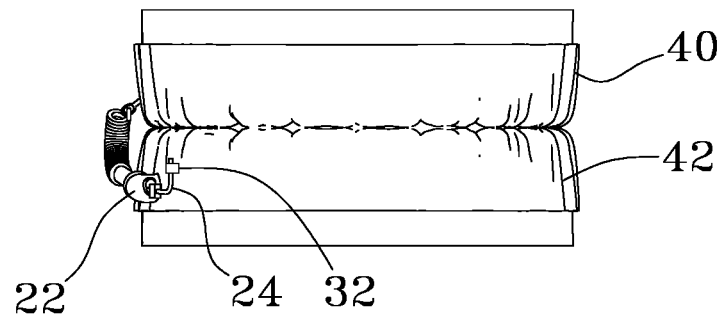
FIG. 6 is a front view of the orthodontic vector force application apparatus installed on a closed dental model for overbite correction.
Figure 7:
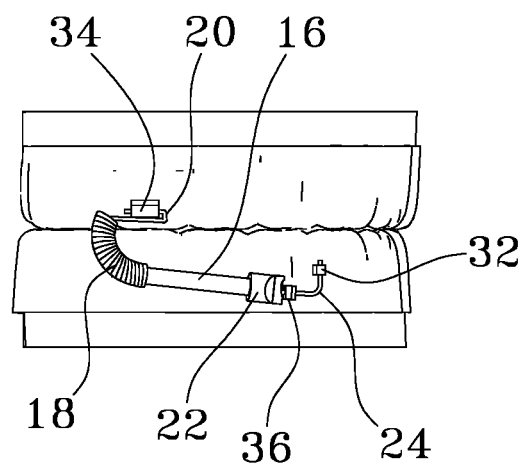
FIG. 7 is a right-side view of the orthodontic vector force application apparatus installed on a closed dental model for overbite correction.
Figure 8:
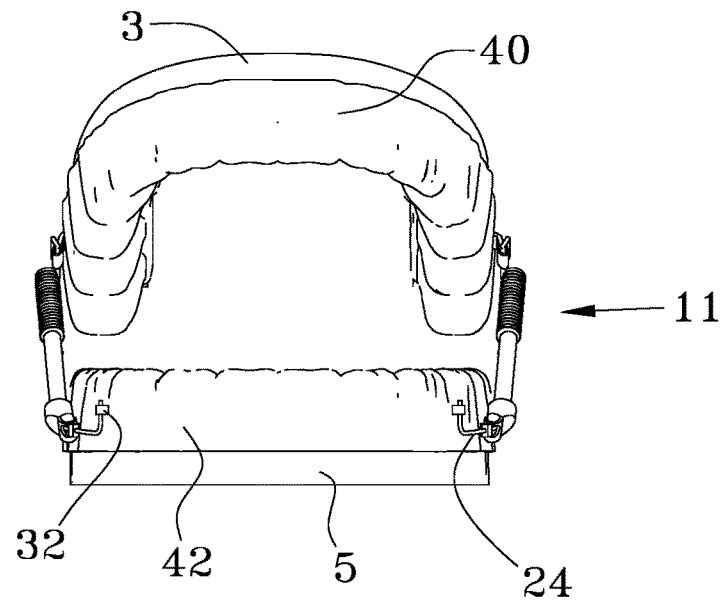
FIG. 8 is a front view of the orthodontic vector force application apparatus installed on an open dental model for overbite correction.
Figure 9:
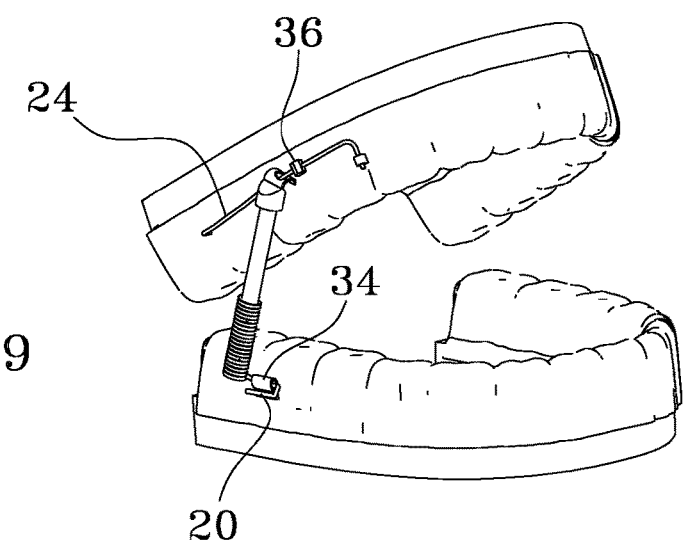
FIG. 9 is a side perspective view of the orthodontic vector force application apparatus installed on an open dental model for underbite correction.

Turning to FIGS. 2 and 8, apparatus 10 is shown in its passive state and can be seen comprised of an upper anchor sheath 40 a lower anchor sheath 42, a pair of curved vector force application means 11 (FIGS. 10-12), a pair of guide wires 24, at two pair of guide wire imbed anchors 32, a pair of attachment wire imbed anchors 34, and a locking stop 36. FIGS. 3, 6 and 7 illustrate the apparatus 10 in its active state.

As can be seen in FIGS. 10-13 the curved intrusive vector force application means 11 of the preferred embodiment is made of rigid linear member 16, a force generating curved vector control module 18, a rear attachment wire 20, and attachment member 22. Preferably, rigid linear member 16 is made of 3/32 (0.093 inch) stainless steel and is elliptical in shape, although in alternate embodiments it my round as well. It has a distal end and a proximal end. Shown in enlarged cross-section, (FIG. 13) the elliptical shape is clearly visible. It should be noted that rigid member 16 can be made of different rigid materials including steel or plastic, and can have other cross sections including circular, square, rectangular, and flat. While illustrated as a tube (hollow), rigid member 16 could also be solid in construction. There are different lengths of the rigid linear member 16 that are used to accommodate the various lengths of dental arches.

The overall length of the device from the distal end of the curved intrusive vector control module 18 to the proximal end of the rigid linear member is in the range of 27 mm to 36 mm. To size the apparatus, with the patient's mouth closed, the dentist makes specific measurements and calculations as discussed herein. The measured distance is designated by dimension arrow Z of FIG. 1.

Curved intrusive vector control module 18, is an elliptical or circular shaped torsion spring, preferably coiled from a wire (preferably round diameter), which is an alloy of NiTi (Nickle Titanium) that is chosen as the preferred material of construction because it may be fabricated with a large diameter wire yet that because of the physical properties of NiTi develps lower return forces upon elastic deformation (bending) without breaking. (Stainless steel springs had high failure rates.) This spring is engineered with its material of construction, wire diameter, shape of coil and its length, such that it in combination with the other curved intrusive vector control module exerts approximately 3.5 ounces of return force (plus or minus 0.5 ounces) when bent at 90 degrees. This was established through a rigorous calibration process at the time of testing and construction that considered and adjusted the four components above. For this reason, the identical vector control module 18 is used in all of the vector force application means. This vector control module 18 in the preferred embodiment is made of 0.039 inch diameter NiTi round wire. (Prior art embodiments use between 0.014 to 0.025 inch diameter stainless steel springs which were prone to work hardening and resultant failure during the corrective period.) The distal end of the spring has a pigtail that extends normally from the linear axis of the unbent spring. This pigtail has been flame annealed to increase the flexibility so that it can be easily bent around the Practical experience has shown that this approximate 3.5 ounces of pressure exerted onto the orthodontic vector force application apparatus by the pair of curved intrusive vector control modules corrects Class II and III malocclusions in approximately four months. Thus small, constant corrective curved vector forces of approximately 3.5 ounces as applied herein, present the optimal method for this type of orthodontic correction.

Using a vector control module 18 with a preset force allows precise control of the realignment process and also allows the device to be set up and configured outside of the patient's mouth. All that is required is a set of castings of the patient's teeth (or a 3D image) and one measurement to establish the length of the rigid linear member 16. The device 2 can be constructed and shipped to the patient ready to be installed. This opens up the opportunities for mail order corrective dental correction devices.

While adjustments may be required, these can actually be made in scheduled increments by the patient themselves. All they need do is look in a mirror to check the angle the vector control module 18 is bent when the jaw is closed. This requires removing the device 2 from the mouth, and moving the locking stops 36 along the guide wires 24 so the vector control module 18 will again be bent at 90 degrees when the jaw is closed fully. (See FIG. 3) Reinsertion of the device and subsequent viewing can proceed through a trial and error process. Once the adjustment is correct, the corrective pressure of the preset 3.5 ounces will be restored. (As the patient's class II or III malocclusion corrects, the jaw slowly realigns itself shifting the location of the vector control module 18 such that it no longer exerts its 3.5 ounces of corrective pressure.)

It is to be noted that different sizes of mouths require different sizes of vector force application means for their orthodontic correction devices. Larger mouth need longer devices. However, there is only one vector control module 18 used in all of the various lengths of vector force application means. This is because the vector control modules are precisely calibrated and constructed to provide a specific 3.5 ounces of return force pressure when bent at 90 degrees. The differences in device lengths are made up by mating the vector control module to different length rigid linear members 16. There are four different assembled vector force application means that range between 27 and 36 mm. (At 27 mm, 30 mm, 33 mm and 36 mm). To determine which length of vector force application means to install, a measurement is made between the front edge of the upper first molars and the back edge of the canine teeth of the lower dental arch. (This is seen as dimension line Z of FIG. 1.) This is generally between 16 mm and 22 mm for most humans. Onto this number is added 12 mm and the sum determines which vector force application means to use.

In the preferred embodiment, the elliptical shape of both the rigid member 16 and curved intrusive vector control module 18 increases patient comfort, since the elliptical shape allows the minor axis of rigid member 16/curved intrusive vector control module 18 to reside in the horizontal plane between the patient's gum line and cheek, while providing increased strength, since the major axis resides generally perpendicular to the gum line. The elliptical shape provides the perfect combination of comfort, food flow, and strength. It is to be noted that circular shaped rigid members are used in alternate embodiments. Variations of the structure of the rigid member 16 and curved intrusive vector control module 18 can accomplish the desired results provided that the end of rigid member 16 that is affixed to curved intrusive vector control module 18 is matingly configured to accept the end of the curved intrusive vector control module 18. For example, a rectangular solid linear member with an elliptical mounting-end (or circular mounting-end for a cylindrical coil) would meet the necessary structural requirements. It is to be noted that each different geometric configuration of the vector control module 18 will have to be specifically designed and tested to ensure that it develops the approximate 3.5 ounces of corrective pressure when bent at 90 degrees.

Curved intrusive vector control module 18 is soldered, welded, or glued to the distal end of the selected length rigid linear member 16, such that curved intrusive vector control module 18 comprises approximately 50-70% of the length of apparatus 10. To give an idea of size, the most common overall length of the assembled vector control module 18 and the rigid linear member is 32 mm. This ratio varies as apparatus 10 will be made in different sizes by attaching different length rigid linear members 16 to the same size, universal vector control module 18 to accommodate different sized mouths. The curved intrusive vector control module will always comprise in the range of 50-70% of the overall length of apparatus 10. This will keep the flex point (located at the approximate midpoint of the torsion spring) of the vector control module 18 to the distal 45-60% of apparatus 10. It is to be noted that the curved intrusive vector forces swing an arc with the inner end of its radius at the flexpoint 100 of the vector control module 18. (FIG. 3) This flexpoint of the vector control module 18 will occur at the midpoint of its unconstrained length. This is between the distal end of the vector control module 18 and the point where the rigid linear member extends into the interior of the proximal end of the torsion spring. The proximal end of the vector control module 18 is stiffened in this region such that its flex point is shifted away from the midpoint of its overall length and towards the distal end of the torsion spring.

In an alternate embodiment, with a circular cross sectional (cylindrical) curved intrusive vector control module, a circular mounting end would be formed on the elliptical rigid member to serve as a connection point to the cylindrical curved intrusive vector control module.

Continuing with FIGS. 10-12, rear attachment wire (pigtail) 20 is an annealed, unwound extension of the wire comprising the curved intrusive vector control module 18. It extends normally from the linear axis of the vector control module 18 and is connected by bending around the wire imbed anchors 34. Attachment member 22 is for adjustable connection with guide wire 24 which is imbededly connected (in either of two ways as disclosed herein) at its proximal (front) and distal (rear) end to one of the anchor sheaths 40 or 42. For quick yet secure attachment with guide wire 24, attachment member 22 has a flat portion 26, which resides at an orientation of approximately 90° from the longitudinal axis of apparatus 10. Attachment member 22 is soldered, welded, or glued to rigid member 16, and can be made of stainless steel, or any rigid, durable material including steel or plastic.

It is to be noted that in alternate embodiments, portion 26 may contain an optional receiving slot 30 that runs from the central orifice 28 to the peripheral edge of the portion 26. This slot 30 allows the apparatus 10 to be removed or installed without removing the guide wire 24 as was previously required with prior art appliances. The slot can be squeezed to close around the guide wire 24 in the installation process.

Moving the flex point of apparatus 10—that is the approximate midpoint of the curved intrusive vector control module 18, to the distal 50-70% of the apparatus's 10 length accomplishes three things: 1) it cannot bend between the teeth to be chewed on and broken, 2) it causes rigid member 16 to reside below the food bolus area 13 (See FIG. 3) to make eating more comfortable, and 3) the curved intrusive force vectors generated by the installed orthodontic apparatus 10 result in correction of the most severe overbites/underbites. Prior art appliances flexing at the midpoint of the appliance and having a hinge at the upper distal end, place linear vectors on the upper and lower jaws, rather than the sweeping arced vectors of the apparatus 10.

In the case of the apparatus 10 used for overbite correction, (FIGS. 2, 3, 4, 6, 7 and 9) the curved intrusive vector force application means 11 is operatively connected to the upper anchor sheath 40 at its rear attachment wire 20 by an attached wire imbed anchor 34. This is a hollow tubular section of metal affixed along its side to a small backing member (preferably a planar member) that is cast into the distal region of the upper anchor sheath with the linear axis residing approximately parallel to the linear axis of the upper anchor sheath 40. (In the preferred embodiment, anchoring teeth clasps that are commonly used to hold retainers in place and are well known and embody this structure.) Its backing member is fully imbedded in the polymer of the anchor sheath such that there are no abrasive sections of the backing member extending from the inner surface of the upper anchor sheath 40. The attached wire imbed anchor 34 is sized for the internal passage of attached wire 20 there through. In this way, the attachment wire 20 may be passed through the inside of the imbed anchor 34 and bent back 180 degrees around the outside of the imbed anchor 34 to secure it to the upper anchor sheath 40.

The curved intrusive vector force application means 11 is operatively connected to the lower anchor sheath 42 by attachment to guide wire 24 as discussed further herein. The guide wire 24 is rigid wire that connects in a spaced configuration along the outside of the lower anchor sheath 42 at proximal and distal sections of the lower anchor sheath 42. This spaced configuration of the guide wire 24 from the side of the lower anchor sheath 42, allows for the adjustment and the sliding movement of the attachment member 22 along the guide wire 2. In its preferred embodiment this guide wire 24 has an approximately right angle bend at its proximal end where it is secured to the guide wire imbed anchor 32. This minimizes interference between the operative parts such as the guide wire imbed anchor 32.

The guide wire imbed anchor 32 utilized at the proximal end of the guide wire 24 and the bottom anchor sheath 42, is essentially another variation of the attached wire imbed anchor 34, but sized accordingly. Its method of attachment to the proximal end of the guide wire 24, however, differs. The proximal end of the guide wire 24 is placed through a bore in the guide wire imbed anchor 32 and mechanically crimped, soldered, glued or permanently affixed by any equivalent means to the guide wire imbed anchor 32. With the bend in the guide wire 24 on one side of the guide wire imbed anchor 32 on the other, the guide wire 24 is securely anchored. The guide wire imbed anchor 32 has a hollow tubular construction, and similar to the attached wire imbed anchor 34 may have a backing member cast into the polymer thickness of the lower anchor sheath 42. In other embodiments a direct implant of the guide wire into the polymer of the anchor sheath (upper or lower) may be utilized. This eliminates the need for connection of the guide wire to the imbed anchors, reducing the number of sharp elements in the patient's mouth. The downfall with this system though, is that in the event of a guide wire breakage, the entire device must be replaced.

The distal end of the guide wire 24 is illustrated attached to the lower anchor sheath 42 by a direct imbed of its plain end (after an approximate 90 degree bend) into the polymer material the anchor sheaths are formed from. At the distal ends of the anchor sheaths the wall thickness is greater than at the proximal end and such a direct imbed is sufficient to retain the distal end of the guide wire 24.

It is to be noted that the guide wire 24 may be affixed to the lower anchor sheath 42 at both its proximal and distal ends by guide wire imbed anchors 32 or it may be affixed to the lower anchor sheath 42 by a direct imbed of the end of the guide wire into a thickened section of the lower anchor sheath 42. Either of the different style of imbeds discussed herein may be utilized in any imbed location of the anchor sheaths and will vary with different manufacturers. The embodiments herein utilize guide wire imbed anchors 32 on the front anchor points of the guide wires 24 and a direct guide wire imbeds on the rear anchor points of the guide wires 24, for illustrative purposes only.

The locking stop 36 of the preferred embodiment is an adjustable locknut with an orifice extending axially through its body perpendicular to the travel of its threaded nut. It's orifice is dimensionally sized for slide positioning along the length of the guide wire 24 so as to constrain the forward movement of the curved intrusive vector force application means 11 along the side of the lower anchor sheath 42 when its nut is tightened against the guide wire 24. The locknut 36 is positioned towards the distal end of the guide wire 24 to maintain the approximate 3.5 ounce corrective pushing pressure of the vector control apparatus 18 (torsion spring) of the apparatus 10 when it is in its active state and the proximal end of the vector force application means 11 abuts the locknut 36. As the patient's malocclusion is slowly corrected and the jaws align better, the curved intrusive vector force application means 11 flex less and the amount of corrective pressure is reduced. This can easily be seen by the patient or the orthodontist as there will no longer be a 90 degree bend in the vector control module 18 with the jaws shut. At this time the device can be removed from the patient's mouth, and locknut 36 loosened, and repositioned along the guide wire 24 and tightened where the vector control module 18 will again bend at 90 degrees when the jaw is shut so that the vector force application means 11 exerts its precise 3.5 oz of pushing pressure when in the active position. It is to be noted that although the pushing pressure of the curved intrusive vector force application means serves to provide the corrective forces to correct the Class II or III malocclusions, an unexpected result of the design of the apparatus is that the pushing intrusive forces also absolutely maintain the upper and lower anchor sheaths 40 and 42 onto the patient's teeth. This was an unanticipated result.

This apparatus 10 provides an enormous improvement over the prior art for several reasons. First, it can be cheaply and accurately constructed with a minimal use of expensive professional input. An accurate impression of the patient's teeth and one measurement is all that is required to construct the apparatus remotely. Second, its corrective pressure is pre-calibrated and limited to approximately 3.5 ounces. There is no need to check the vector control module's corrective pressure upon initial installation. Essentially, the apparatus can arrive in the mail and the patient can immediately install in privacy. Third, it does not require an Orthodontist to adjust. The patient can visually see their progress and when adjustment is needed. Orthodontist visits are greatly reduced. Fourth, it does not require the direct attachment to a set of braces affixed onto the patient's teeth, allowing those without braces for Class I malocclusions to wear them. Fifth, it is removable for temporary periods by the patient themselves. Sixth, it does not deliver its force straight along its axis to the distal side of the molars, rather it imparts a curved intrusion vector force so as to retain the anchor sheaths on the patient's teeth.

Figure 5:
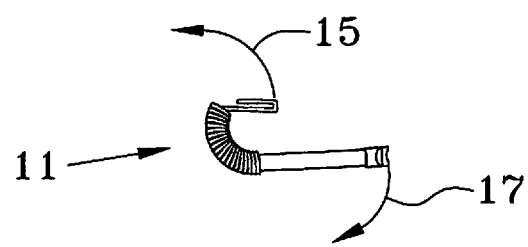
FIG. 5 is a left-side view of the orthodontic vector force application apparatus in its flexed state; the curved rays illustrating the path required for the appliance to return to its passive (unflexed) state.

The apparatus works in the following manner. The attachment wire 20 is connected directly to the vector control module 18 without a hinge, allowing apparatus 10, as shown in FIG. 3, to return to its passive, pre-installed state (FIG. 2) in a sweeping motion 15. (FIG. 5) This lifts up on the front (closest to the mouth opening) of the molar tube, while the sweeping force is placed on the mandible as ray 17 illustrates. This curved intrusive vector force thus prevents the upper jaw from tipping therein preventing dislodging of the front of the anchor sheath. This was a problem with the linear vector forces applied through the prior art orthodontic apparatuses. This is best illustrated in FIG. 5 which shows apparatus 10 in its installed shape—that is, the same shape that can be seen in FIG. 3. The non-linear rays, 15 and 17, indicate the direction apparatus 10 moves in order to return to its pre-installed/passive state. As can be seen, the distal and proximal ends of the curved intrusive vector force application apparatus 10 apply their sweeping corrective forces in arcs having a radius originating at the approximate midpoint of the flexed (bent) curved vector control module 18. These rays 15 and 17, indicate the curved intrusive vector forces that the apparatus imparts to the teeth and jaws. While FIG. 5 is not a free body diagram, it is not hard to imagine while looking at FIG. 5 in conjunction with FIG. 3, how apparatus 10 lifts up on the front of the molar tube causing the roots (not illustrated) of the upper molars to tip toward the back of the mouth prior to the whole tooth moving distal. Since the molars are connected to the front teeth via the guide wire 24 anchored into the lower anchor sheath 42, intrusive and backward curved vectors are placed on the upper incisors. The mandibular front teeth receive an equal and opposite force, shown in FIG. 5 as ray 17 illustrated pushing downwards and forward on these teeth, intruding them to compensate for their overbite condition.

Functionally, as installed in FIGS. 2-8, apparatus 10 will reposition the upper dental arch 12 by placing forces on the upper molars (maxillary), causing their root tips (not illustrated) to move backwards (that is towards the back of the throat) first, putting curved intrusive vector forces on the front upper and lower incisors, keeping the apparatus 10 on the patient's teeth and over a period of months correcting even the most severe overbites (Class II malocclusions).

The majority of this disclosure discusses and illustrates use of the apparatus 10 for treatment of a Class II malocclusion or overbite condition. For use in a Class III malocclusion or underbite condition, (FIG. 9) the above apparatus 10 is simply inverted (or worn upside down) with respect to the connection of the guide wire 24 and the vector force application means 11 to the anchor sheaths. Here the guide wire 24 is affixed to the upper anchor sheath 40 and the distal end of the curved intrusive vector force application means 11 is affixed to the rear of the lower anchor sheath 42. Connection of the curved intrusive vector force application means 11 to the guide wire 24 is identical where attachment member 22 at the proximal end of the curved intrusive vector force application means 11 slides onto the guide wire 24 via its receiving slot 29 (which is squeezed to close) and the pressure adjusted via locknut 36. However, the rear attachment wire 20 of the curved intrusive vector force application means 11 is connected to the lower anchor support 42 by an imbed anchor around which the rear attachment wire 20 is bent around.

Once installed, appliance 10 will push the lower dental arch 14 backwards, and provide pushing vectors on the upper front teeth, resulting in the repositioning of the maxilla to the desired position. Functionally, in this configuration apparatus 10 will reposition the lower dental arch 5 by placing forces on the lower molars, causing their root tips (not illustrated) to move distally (that is towards the front of the throat) first, putting intrusive forces on the front upper and lower incisors, and over a period of months correcting even the most severe Class III malocclusions.

Although not illustrated herein, the anchor sheaths 40 or 42 need not extend over all of the teeth in either of the dental arches, rather it can resemble a partial aligner or partial plate. The anchor sheaths need only encapsulate enough teeth to gently urge the jaws into their corrective position without affecting the spacing or slat of the encapsulated teeth.

The method of applying curved vector forces for the correction of Class II or Class III malocclusions is best detailed in the following steps of:

Measuring the distance between the front of the upper arch first molar and the back edge of the lower arch canine tooth in the patient's mouth and determining the size of the orthodontic vector force application apparatus;

Selecting the proper size of rigid linear member for that size of orthodontic vector force application apparatus;

Prepare and test a curved intrusive vector force control module (torsion spring) with a rear attachment wire, that exerts approximately 3.5 ounces of return force when bent at 90 degrees about its approximate midpoint;

Assembling two curved intrusive vector force application means by affixing a proximal end of the 3.5 ounce vector control module to the distal end of the selected rigid linear member; (in this configuration the midpoint (flexpoint) of the curved intrusive vector force control module will lie in the distal region 50-70% of the distance away from its proximal end);

Obtaining an accurate profile of a patient's upper and lower dental arches (this step can be done earlier in the sequence of steps);

Constructing a pair of first and second anchor sheaths that matingly conform to the profile of a patient's upper and lower dental arches, with guide wire imbed anchors and attached wire imbed anchors therein at reinforced regions of the anchor sheaths (optionally as discussed herein, there may a direct imbed of the guide wires into the first anchor sheath eliminating the need for guide wire imbed anchors— if this is the case the following two steps shall be skipped);

Installing a locking stop onto each of the linear guide wires;

Assembling the removable first anchor sheath by connecting a pair of linear guide wires affixed at their distal and proximal ends to the guide wire imbed anchors in the first anchor sheath and extending from the anchor sheath's sides;

Installing the distal end of each curved intrusive vector force application means to the guide wire imbed anchors on the second anchor sheath by bending their rear attachment wires about the wire imbed anchors;

Installing the proximal end of each curved intrusive vector force application means to the guide wires on the first anchor sheath by putting the attachment member of the linear member around the guide wire between the locking stop and the distal ends of the guide wires;

Adjusting and lock the position of the locking stop along the guide wires so as to abut the attachment member when the first and second anchor sheaths are brought into mating contact (jaws closed) and the intrusive vector force control module is bent 90 degrees;

Installing over a portion of the teeth in a first dental arch, the removable first anchor sheath while installing over a portion of the teeth in a second dental arch, the removable second anchor sheath.

The following steps are optional steps that can be done at a time of fitting by an orthodontist, although the apparatus is constructed so as to be functional and correctly adjusted after assembly.

Shutting the patient's jaw such that the first and second anchor sheaths are in mating contact, and viewing the bend angle of the vector force control module; and Adjusting the forward stop position of the locking stop on the guide wire to provide a 90 degree bend angle of the vector force control module when the patient's jaw is shut.

While certain features and aspects have been described with respect to exemplary embodiments, one skilled in the art will recognize that numerous modifications are possible. For example, while various methods and processes described herein may be described with respect to particular structural and/or functional components for ease of description, methods provided by various embodiments are not limited to any particular structural and/or functional architecture, but instead can be implemented on any suitable dental appliance configuration. Similarly, while certain functionality is ascribed to certain system components, unless the context dictates otherwise, this functionality can be distributed among various other system components in accordance with the several embodiments.

Consequently, although several exemplary embodiments are described above, it will be appreciated that the invention is intended to cover all modifications and equivalents within the scope of the following claims.

Having thus described the invention, what is claimed as new and desired to be secured by Letters Patent is as follows:

1. A reversible, removeable, orthodontic vector force application apparatus for the treatment of Class II and Class III malocclusions only, comprising:
    a first anchor sheath custom formed for frictional engagement over at least a portion of a first dental arch;
    a second anchor sheath custom formed for frictional engagement over at least a portion of a second dental arch,
    a pair of curved vector force application means with a calibrated, preset shared amount of return force pressure when bent to 90 degrees, each said vector force application means having a proximal end and a distal end;
    a pair of guide wires connected to said first anchor sheath and each extending along a side of said first anchor sheath,
    wherein each said proximal end of said each vector force application means is slidingly affixed to one of said guide wires, and each said distal end of said vector force application means is rigidly affixed to said second anchor sheath; and
    wherein for treatment of said class II malocclusion said first dental arch is an upper dental arch and said second dental arch is a lower dental arch; and
    wherein for treatment of class III malocclusion said first dental arch is a lower dental arch and said second dental arch is an upper dental arch; and
    wherein for class II malocclusion treatment said first anchor sheath is a lower anchor sheath fitted for frictional attachment over at least some of a set of teeth in a lower dental arch and said second anchor sheath is an upper anchor sheath fitted for frictional attachment over at least some of a set of teeth in an upper dental arch; and
    wherein for class III malocclusion treatment said first anchor sheath is an upper anchor sheath fitted for frictional attachment over at least some of a set of teeth in an upper dental arch and said second anchor sheath is a lower anchor sheath fitted for frictional attachment over at least some of a set of teeth in a lower dental arch.

2. The removable orthodontic vector force application means of claim 1 wherein said calibrated, preset shared amount of return force pressure of said pair of vector force application means is approximately 3.5 ounces.

3. The removable orthodontic vector force application means of claim 2 wherein each of said vector force application means is comprised of a vector control module connected rear end of a rigid linear member.

4. The removable orthodontic vector force application means of claim 3 wherein said vector control module is a torsion spring made of a Nickle Titanium alloy, said torsion spring having an annealed distal end extending perpendicular to a linear axis of said spring.

5. The removable orthodontic vector force application means of claim 4 wherein said vector force control module is made of 0.039 inch diameter wire.

6. The removable orthodontic vector force application means of claim 4 further comprising a pair of attachment wire imbed anchors in said second anchor sheath wherein each said vector control module is affixed to said second anchor sheath by attachment of said annealed end of each said torsion spring to one of said wire imbed anchors.

7. The removeable, orthodontic vector force application apparatus of claim 4 wherein each of said vector force application means has an attachment member affixed to a front end of each of said rigid linear member, each of said application means slidingly attached to each of said guide wires.

8. The removable, orthodontic vector force application apparatus of claim 4 wherein said torsion spring is elliptical in cross section.

9. The removable, orthodontic vector force application apparatus of claim 4 wherein said torsion spring is circular in cross section.

10. The removeable, orthodontic vector force application apparatus of claim 1 further comprising at least one adjustable locking stop frictionally engagable along each of said guide wires.

* * * * *